United States Patent
Stalder et al.

(10) Patent No.: US 11,412,993 B2
(45) Date of Patent: Aug. 16, 2022

(54) SYSTEM AND METHOD FOR SCANNING ANATOMICAL STRUCTURES AND FOR DISPLAYING A SCANNING RESULT

(71) Applicant: DENTSPLY SIRONA inc., York, PA (US)

(72) Inventors: Severin Stalder, Zürich (CH); Markus Berner, Bulach (CH); Konrad Klein, Heidelberg (DE)

(73) Assignee: DENTSPLY SIRONA Inc., York, PA (US)

( * ) Notice: Subject to any disclaimer, the term of this patent is extended or adjusted under 35 U.S.C. 154(b) by 394 days.

(21) Appl. No.: 15/742,556

(22) PCT Filed: Jul. 8, 2016

(86) PCT No.: PCT/EP2016/066259
§ 371 (c)(1),
(2) Date: Jan. 8, 2018

(87) PCT Pub. No.: WO2017/005897
PCT Pub. Date: Jan. 12, 2017

(65) Prior Publication Data
US 2018/0192964 A1    Jul. 12, 2018

(30) Foreign Application Priority Data
Jul. 8, 2015    (DE) .......................... 102015212806.7

(51) Int. Cl.
*A61B 5/00* (2006.01)
*A61B 5/107* (2006.01)
(Continued)

(52) U.S. Cl.
CPC .......... *A61B 5/7425* (2013.01); *A61B 5/0088* (2013.01); *A61B 5/1077* (2013.01);
(Continued)

(58) Field of Classification Search
CPC ... A61B 5/7425; A61B 5/6886; A61B 5/4547; A61B 90/50; A61B 90/361; A61B 5/743;
(Continued)

(56) References Cited

U.S. PATENT DOCUMENTS 6,503,195 B1    1/2003 Keller
7,463,757 B2    12/2008 Luo
(Continued)

FOREIGN PATENT DOCUMENTS

CN    103886145 A    6/2014
JP    2010259497 A * 11/2010
(Continued)

OTHER PUBLICATIONS

K. Kiyokawa, M. Billinghurst, B. Campbell, and E. Woods, "An occlusion capable optical see-through head mount display for supporting co-located collaboration," Proceedings of The Second IEEE and ACM International Symposium on Mixed and Augmented Reality, pp. 1-9 (Year: 2003).*
(Continued)

*Primary Examiner* — Ashley K Buran
*Assistant Examiner* — Amy J Shafqat
(74) *Attorney, Agent, or Firm* — Dentsply Sirona Inc.

(57) ABSTRACT

A system for scanning anatomical structures and for visualizing the scanning result, wherein the system includes an intraoral scanner, which intraorally captures an image of the anatomical structures, an extraoral detection unit, which detects a spatial position of the intraoral scanner relative to an observer or a person conducting the scan, and a computing unit, which, during the scanning procedure, connects the scanner with a screen and the detection unit and generates a scanning result based on the intraorally captured image of the anatomical structures and the detected spatial position of the intraoral scanner relative to the observer, and which,
(Continued)

during pauses in the scanning procedure, estimates the position, orientation and scaling of the anatomical structures and, as a scanning result, generates an image of the anatomical structures corresponding to the estimation, and wherein the screen displays the scanning result generated by the computing unit.

16 Claims, 6 Drawing Sheets

(51) Int. Cl.
*A61B 90/00* (2016.01)
*A61B 90/50* (2016.01)
*A61B 17/00* (2006.01)
*A61B 34/20* (2016.01)

(52) U.S. Cl.
CPC .......... *A61B 5/4547* (2013.01); *A61B 5/6886* (2013.01); *A61B 5/743* (2013.01); *A61B 90/361* (2016.02); *A61B 90/50* (2016.02); *A61B 2017/00216* (2013.01); *A61B 2034/2048* (2016.02); *A61B 2034/2065* (2016.02); *A61B 2090/365* (2016.02); *A61B 2090/372* (2016.02); *A61B 2090/502* (2016.02)

(58) Field of Classification Search
CPC ................ A61B 5/0088; A61B 5/1077; A61B 2017/00216; A61B 2034/2065; A61B 2034/2048; A61B 2090/372; A61B 2090/502; A61B 2090/365
See application file for complete search history.

(56) References Cited

U.S. PATENT DOCUMENTS

| | | | |
|---|---|---|---|
| 7,751,606 B2 | 7/2010 | Luo | |
| 8,556,625 B2 | 10/2013 | Lovely | |
| 9,414,750 B2 | 8/2016 | Lovely | |
| 9,517,041 B2* | 12/2016 | Melman | A61B 6/4007 |
| 9,606,992 B2* | 3/2017 | Geisner | G09G 3/003 |
| 10,504,386 B2* | 12/2019 | Levin | G06F 3/0481 |
| 2002/0006217 A1* | 1/2002 | Rubbert | A61C 7/00 |
| | | | 382/131 |
| 2005/0020910 A1 | 1/2005 | Quadling | |
| 2005/0123180 A1 | 6/2005 | Luo | |
| 2005/0170309 A1* | 8/2005 | Raby | A61C 7/146 |
| | | | 433/24 |
| 2007/0013461 A1 | 1/2007 | Montena | |
| 2007/0172101 A1 | 7/2007 | Kriveshko | |
| 2007/0238981 A1 | 10/2007 | Zhu | |
| 2009/0042168 A1 | 2/2009 | Luo | |
| 2012/0056993 A1 | 3/2012 | Luqman | |
| 2013/0242262 A1 | 9/2013 | Lewis | |
| 2014/0018679 A1 | 1/2014 | Chen | |
| 2015/0350517 A1* | 12/2015 | Duret | A61B 1/00009 |
| | | | 348/66 |
| 2016/0034583 A1 | 2/2016 | Agarwal | |
| 2017/0319054 A1* | 11/2017 | Miller | A61B 1/0684 |

FOREIGN PATENT DOCUMENTS

| | | |
|---|---|---|
| JP | 2010259497 A | 11/2010 |
| WO | 2004100067 A2 | 11/2004 |
| WO | 2010067267 A1 | 6/2010 |
| WO | 2014120909 A1 | 8/2014 |
| WO | 2015181454 A1 | 12/2015 |

OTHER PUBLICATIONS

M. Ozuysal et al; Feature Harvesting for Tracking-by-Detection; European Conference on Computer Vision, 2006.
D. Wagner et al; Robust and Unobtrusive Marker Tracking on Mobile Phones; Technical Report, Graz University of Technology.
Hartley and Zissermann; Multiple View Geometry in Computer Vision, Cambridge University Press.
Ender and Mehl; Influence of scanning strategies on the accuracy of digital intraoral scanning systems; International Journal of Computerized Dentistry, 2013.
T. Weise et al; In-hand Scanning with Online Loop Closure; ICCV Workshops, 2009.
Kligus, T. et al; Mobile markerless augmented reality and its application in forensic medicine, International Journal of Computer Assisted Radiology and Surgery, 2015.
International Search Report; PCT/EP2016/066259; Oct. 12, 2016 (completed); dated Oct. 19, 2016.
Written Opinion of the International Searching Authority; PCT/EP2016/066259; Oct. 12, 2016 (completed); dated Oct. 19, 2016.
International Preliminary Report on Patentability; PCT/EP2016/066259; Oct. 12, 2016 (completed); dated Oct. 19, 2016.
S. Rusinkiewicz and Marc Levoy: Efficient Variants of the ICP Algorithm, 3-D Digital Imaging and Modeling, 2001.

* cited by examiner

SYSTEM AND METHOD FOR SCANNING ANATOMICAL STRUCTURES AND FOR DISPLAYING A SCANNING RESULT

TECHNICAL FIELD

The present invention relates to a system for scanning anatomical structures, such as the teeth or the jaw of patients, in order to create an optical, intraoral impression and to display and visualize the scanning results, and an associated method.

BACKGROUND OF THE INVENTION

The present invention particularly relates to interactive and incremental scanning. During the scanning procedure, individual scans are combined to form a model of an anatomical structure. This type of scan, as described for example in "S. Rusinkiewicz and Marc Levoy: Efficient variants of the ICP algorithm, 3-D Digital Imaging and Modeling, 2001", is performed with a scanner that is separate from a viewer or an observer or a person conducting the scan and from the screen. The scanner is guided by hand with the aim of creating a gapless and high-precision optical impression as quickly as possible. In order to achieve this objective, a simple and intuitive visualization of the current scanning result is extremely important. The proposed invention displays the scanning results in a natural manner and thus simplifies the handling of the scanner.

Today, when scanning with the CEREC method, a dentition of a patient is displayed as a scanned model on a screen in the vicinity of the patient. When scanning, a person conducting the scan, such as a dentist, is in a constant state of dilemma about where to look. The quality of the already scanned model can be seen on the screen. In particular gaps in the model, for example, can also be recognized. To close these gaps in the model and to guide the scanner to the right place, the gaze must be directed back to the patient's dentition and to the scanner. A great deal of experience and practice are needed to establish the correlation between the model and the patient's dentition. As an additional aid in existing systems, a rather annoying acoustic signal is emitted as non-visual feedback about the success of the scan.

The present invention can be established in the field of augmented reality, but differs significantly from the conventional augmented reality applications.

There are a large number of augmented reality applications in which externally invisible views are overlaid. Mini/BMW, for example, is planning a type of "X-ray glasses" to fade out the masking effects of the vehicle body and to enable a wider field of view. There are similar systems for autopsies. For example, there is a system described in "Kilgus, T. et al: Mobile markerless augmented reality and its application in forensic medicine, International Journal of Computer Assisted Radiology and Surgery, 2015", which displays multi-modal data, such as X-ray data, on a movable screen. To do this, an external depth camera is used to detect the spatial position of the screen. However, this system does not create an incremental model. The augmented screen only displays existing data in a spatially meaningful manner.

There are similar applications for augmented reality in endoscopy. The endoscopic instruments have to be navigated to a specific point with precision, which can be displayed in a simplified manner with the aid of augmented reality. Important navigation points and the planned intervention path are interactively overlaid into the endoscopic image. On the other hand, there is no interactive and incremental creation of a model of the anatomical structures. Therefore, the augmented display in endoscopy helps exclusively in the rough navigation of the instruments on a pre-planned intervention path.

The invention presented here differs from other augmented reality applications also in the manner in which the position of the artificial data to reality (live view of the real world surroundings) is determined. This positioning is performed very precisely and in a simple manner via the position of the scanner and the scanning result.

For dental applications, US 2007/0172101 A1 describes a similar system. According to this invention, a three-dimensional model is superimposed over a two-dimensional image. The two-dimensional image originates from an intraoral camera. The three-dimensional model is the combination of the three-dimensional images of the intraoral scanner. Both views were originally created from the same viewing angle. The position of the viewer or the screen has no effect on the visualization.

Depending on the application, the model is the important result of the scanning procedure. In certain situations a single scan can be insufficient. A scan in specific, difficult to measure areas, for example, can be incomplete (pitted), faulty or noisy. Such insufficiencies can possibly be overcome by combining multiple scans, which were taken from different viewing angles for example. The assessment of the model as a result of the scanning procedure is therefore extremely important.

The method of merging is typically a method that aligns the three-dimensional shape of the scan and the model with one another, typically a variant of the ICP (Iterative Closest Point) method. During merging, the new scan is added to the already scanned scan data, i.e. applied in such a way that the new scan data conforms to the existing scan data with minimal errors. It is then continuously necessary to check whether this addition was also successful. To do this, the found minimum error or the degree of overlap, for example, is examined. The found minimum error must typically be sufficiently small and the degree of overlap must be sufficiently large. if such criteria are met, the new scan will also become part of the model, otherwise it must, at least for the moment, be discarded.

There are a variety of reasons why the addition of scans to the model is sometimes not successful. Some of these reasons are:

The user moved the scanner too fast, so that the new scan does not overlap or does not overlap enough with the model.

The user moves the scanner in such a way that the object to be scanned is located outside the scan range of the scanner.

The scan data includes too much interference, so that the error in the ICP is too large.

The scanned structure is not rigidly cohesive and has deformed. The new scan can therefore not match the model. In the described application, such parts are the tongue or the cheek, for example, which can move independently of the rigid teeth.

If a scan cannot be added to the model for any reason, the scanner can be used only to a limited extent as an aid to display the virtual model at the correct position relative to the anatomical structure. This is because there is no information regarding the location of the current scan relative to the model.

For hand-guided, incremental scanning, the user has to ensure that new scans can be successfully added to the model. If the current scan cannot be added to the model, the user has to take corrective measures and move the scanner in such a way that a new scan can be added to the model. This situation represents a problem in the operation for the user, because the continuous scanning procedure is interrupted. Particularly in this type of situation, it is very helpful if the virtual model is displayed correctly on the anatomical structure. The user can thus move the scanner more easily to the existing model. In this type of situation, the current scan will also be overlaid at the correct location.

There are other situations as well, in which the virtual model is to be displayed at the correct location and the scanner can be included only to a limited extent as an aid.

For example, the scanning procedure and the assessment of the scanned model cannot take place at the same time. Depending on the scanning technology being used, the scanner projects visible light onto the teeth, which interferes with the visualization of the scan model. In such a case it may be necessary to interrupt the scanning procedure in order to evaluate the model more accurately.

WO 2004/100067 A2 describes a system, which displays a direct scanning result in such a way that the object to be scanned and the scanning result are visible at a single glance to the person conducting the scan. To do this, the scanner is used as an aid for proper display in a manner quite similar to the system used in laparoscopic surgery described in U.S. Pat. No. 6,503,195 B1. Neither WO 2004/100067 A2 nor U.S. Pat. No. 6,503,195 B1 describe any assistance for the user when individual scans are compiled into a larger model. This compiling is particularly difficult for the user if the current scan cannot be added to the existing model. Our invention describes a system for critical moments such as those. WO 2004/100067 A2 does not mention these critical moments.

WO 2015/181454 A1 describes a system that overlays a scanning result or additional information onto the anatomical structures in the mouth of a patient. The images of the intraoral scanner and the overview camera are superimposed on one another by bringing three-dimensional point clouds into alignment. The description provides no indication that the overview cameras of the augmented reality glasses mentioned in the description permit a calculation of a point cloud of the anatomical structures sufficiently accurate to perform a precise superposition.

US 2012/0056993 A1, WO 2010/067267 A1 and WO 2014/120909 A1 are further documents that describe systems for visualizing scanning results.

SUMMARY OF THE INVENTION

The object of the present invention is to provide a system for scanning anatomical structures and visualizing the scanning result, and an associated method. The visualization of the scanning result is intended to allow easier handling of the scanner. A superposition of the scanned anatomical structures with the digital model that is as precise as possible should additionally also be possible during interruptions in the scanning procedure.

A system for scanning anatomical structures and for visualizing the scanning results is provided, wherein the system comprises the following: an intraoral scanner that intraorally captures an image of the anatomical structures; an extraoral detection unit that detects the spatial position of the intraoral scanner relative to an observer, and a computing unit that, during the scanning procedure, connects the scanner with a screen and the detection unit, and generates a scanning result based on the intraorally captured image of the anatomical structures and the detected spatial position of the intraoral scanner relative to the observer, and that, during pauses in the scanning procedure, estimates the position, orientation and scaling of the anatomical structures and, as a scanning result, generates an image of the anatomical structures corresponding to the estimation, wherein the screen displays the scanning result generated by the computing unit.

In particular the use of video-capable 3D surface imaging for the real-time superposition of reality (a live view of the surroundings) with recorded 3D data, using the recording device to determine the transformation chain between 3D data and user field of view, is possible according to the invention.

An anatomical structure can in particular include teeth as a scan template that are scanned and examined by a dentist as the person conducting the scan. In an advantageous manner, using the system according to the invention the dentist can view the real teeth and the scanned teeth superimposed on one another and make a diagnosis. To make the superposition of the scanned anatomical structures with the digital model as precise as possible even during interruptions in the scanning procedure, parameters such as position, orientation and scaling of the real anatomical structure and the overlaid virtual model of the anatomical structure are brought into correlation.

In contrast to the system known from WO 2015/181454 A1, the present invention advantageously proposes the use of the scanner as an aid during scanning, in order to estimate a correlation for a precise superposition much more accurately than was done previously. Furthermore, according to the invention, the properties that are required for correlation are selected from among a variety of properties during the successful addition of scans to the model. Therefore, not only the three-dimensional shape is brought into correlation; two-dimensional properties, for example, can be merged as well. Properties that were not directly detected by the scanner, but are only in the vicinity thereof, can also be used to achieve a precise match. This is possible, because the relationship between these properties and the position of the virtual model during scanning is known.

The screen is preferably incorporated in augmented reality glasses, so as to be located directly within the field of view of a person conducting the scan, while the detection unit is provided in the immediate vicinity of the screen and ideally rigidly connected thereto. A dentist can thus examine the teeth of a patient in the most simple manner, without having to move his eyes back and forth between the patient's mouth and a screen. In particular, the detection unit and the screen can be rigidly mounted near the head of the person conducting the scan.

The system preferably further comprises an eye camera, which detects the movements of the eyes and/or the head of the person conducting the scan relative to the detection unit and the screen, wherein the computing unit generates the scanning result displayed on the screen adapted to the detected movements. Due to the eye camera, a recalibration of the screen can be avoided and usable angle range can be increased.

The system preferably further also comprises position sensors, which detect the movements of the person conducting the scan. It also comprises position sensors near the scanner, which detect the movements of the scanner. The computing unit takes the detected movements into account when generating the scanning results displayed on the screen. The position sensors also allow the visualization of the scanning result displayed on the screen to be even more accurate than it would be without them. The robustness of the system is increased as a result of the position sensors.

The computing unit advantageously performs transformations between coordinate systems. The coordinate systems include a coordinate system of the intraorally captured image, a coordinate system of the scanner, a coordinate system of the detection unit and a coordinate system of the screen. The coordinate systems can further respectively include a coordinate system of the screen for a left eye and a right eye of the person conducting the scan, and respectively a coordinate system for a left eye and a right eye of the person conducting the scan. As a result of the transformations between the coordinate systems, a precise, spatially meaningful visualization of a scanning result can be carried out on the screen as a superimposed image.

The screen preferably also displays information related to successful scanning. As a result, it is always ensured that an unsuccessful scan can be recognized immediately.

Particularly preferably, the computing unit processes the image of the anatomical structures intraorally captured by the scanner in such a way that it is displayed on the screen near the head of the scanner. The scanner can therefore be used as a virtual mirror. In this context virtual means that there is no conventional optical mirror, but rather that the recorded image is displayed near the head of the scanner and is visible only by means of the screen. The mirror is not physically present—the functionality of a mirror can be seen only by means of the display on the screen.

The detection unit can, for example, be a simple 3D camera, which detects the three-dimensional position of the scanner, or even only a 2D camera, with which, under certain conditions, the three-dimensional position of the scanner can be determined as well.

Optical position markers are advantageously provided on the scanner. With the position markers, it is possible to determine the position of the scanner by means of the detection unit near the scanner in a particularly simple manner using an ordinary 2D camera as the detection unit, by determining a distance between the position markers with the 2D camera and inferring the distance of the scanner to the 2D camera on the basis of this determined or measured distance.

The invention further provides a method for scanning anatomical structures and for visualizing the scanning result using a system configured according to any of the preceding claims, characterized by the following method steps: capturing an image of the anatomical structures with the intraoral scanner, detecting the spatial position of the intraoral scanner, superimposing the 2D and/or 3D image captured by the scanner by means of a transformation between the coordinate systems, and displaying the generated scanning result on the screen.

With the method according to the invention, it is possible to improve a visualization of a scanning result on a screen and to facilitate the further use of the visualization.

In particular, a scanning result is formed by merging individual images of the anatomical structures captured intraorally by the scanner. Thus, in the event that the anatomical structures are teeth, an entire jaw can be displayed without any additional effort.

The respective position of the scanner is preferably tracked and recorded by means of the extraoral detection unit. A visualization of a scanning result together with a visualization of the position of the scanner together with an extraorally captured image is thus possible.

The respective position of the scanner is preferably tracked by using position markers on the scanner. The use of position markers on the scanner allows a precise determination of the position of the scanner and therefore precise tracking of the scanner.

The computing unit preferably estimates the position, orientation and scaling of the anatomical structures by means of an invasive or a non-invasive method, wherein the invasive method includes an attachment of markers or some other tracking sensor on the anatomical structure to be scanned, and the non-invasive method includes a pairing of optical two-dimensional or three-dimensional properties of the anatomical structure. For improved estimation of the position, orientation and scaling of the anatomical structures, an automated learning phase also passes through the computing unit for automatic learning. This means that, for improved estimation of the position, orientation and scaling of the anatomical structures, during a successful addition of scans to a model the computing unit passes through a learning phase, which helps to display the virtual model during pauses in the scanning procedure, wherein transformations between the virtual model and the properties on the anatomical structures or in proximity thereto are known or can be learned during a successful scan, and wherein two- or three-dimensional properties can be selected in order to track the virtual model in a stable and robust manner during pauses in the scanning procedure. By means of this estimation and learning, more accurate images of anatomical structures can be obtained than was previously possible.

The image of the anatomical structures captured intraorally by the scanner and/or the scanning result is displayed on the screen relative to the position of the scanner in an advantageous manner. A comprehensive and precise visualization of a scanning result is thus possible.

According to the invention, therefore, this results in the advantage of a fast, uncomplicated and precise scanning of anatomical structures, and a visualization of a scanning result that is comfortable for a user.

BRIEF DESCRIPTION OF THE DRAWINGS

The stated and further features and details of the invention will become clearer to a person skilled in the art in this field from the following detailed description and the attached drawings, which illustrate the features of the present invention on the basis of an example, and wherein.

DETAILED DESCRIPTION OF THE INVENTION

The present invention will be explained in further detail in the following on the basis of preferred embodiments and with reference to the figures.

Figure 1:
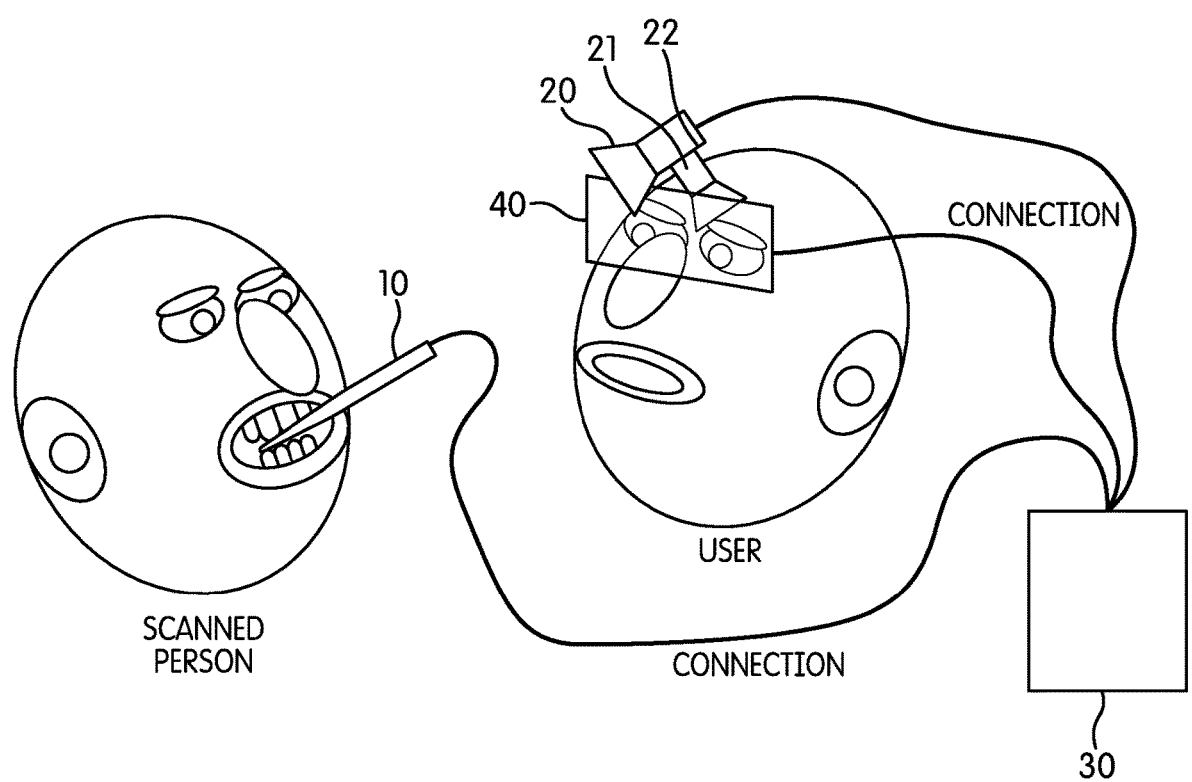
FIG. 1 shows a system according to the present invention.

FIG. 1 shows a system, in which a screen 40 in the form of augmented reality glasses is placed directly into the field of view of a person conducting the scan. Real teeth as an anatomical structure and a scanning result are visible at a single glance to the person conducting the scan. In a display unit, a screen 40 superimposes a virtual content into the real field of view (augmented reality).

Augmented reality glasses will soon be commercially available. The present invention can be implemented with a Microsoft HoloLens, for example. In this case, the detection unit 20 for the spatial position of the scanner is a 3D depth camera with an associated 2D color image. Both the screen 40 and the computing unit 30 are integrated into the glasses.

Figure 2:
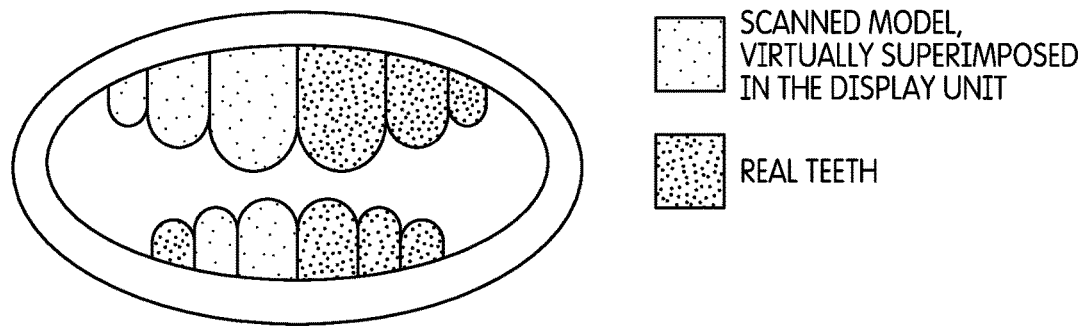
FIG. 2 shows a display of a screen of the system according to the present invention.

Scanning results and helpful hints, which are fitted into the surroundings, are visible on the screen 40. The teeth to be scanned as an anatomical structure, already acquired teeth and a scanner 10 (also referred to herein interchangeably as an intraoral scanner) are visible at a single glance and superimposed on one another, as can be seen in FIG. 2.

The system comprises the screen 40, on which scanning results and information can be seen, as a central element. The screen 40 allows the user, the person conducting the scan, to see both the teeth as a scan template and the scanning results at the same time and superimposed on one another.

The screen 40 can be designed in a variety of ways. In the case of a semi-transparent screen as a first example, for example, a virtual content is superimposed on reality (a live view of the surroundings) and the live view of the surroundings appears at most slightly dimmed. In the case of a completely virtual screen as a second example, the virtual content is superimposed on a video of the surroundings. This video is recorded from a natural point of view. The virtual content can, however, also be projected directly onto the retina of a person conducting the scan.

Of course, any combinations of the first example and the second example are also conceivable: the viewed surroundings can also be superimposed in a semi-transparent manner and/or superposition can be carried out by not showing the same content on the two screens in front of the eyes. It is also conceivable that the degree of superposition is set individually by each user.

The system further comprises a detection unit 20, which detects the spatial position of the intraoral scanner and is provided in direct proximity to the screen 40 and preferably rigidly connected to said screen 40. A two- or optionally a three-dimensional camera is often integrated in augmented reality glasses. This camera can function as a detection unit 20 and capture the scene from a point of view similar to that of the user of the scanner 10 as the person conducting the scan. The detection unit 20 is used to detect the spatial position of the scanner 10 and to display the intraoral scanning result at a specific location, relative to the intraoral scanner. It is useful, for example, to superimpose the virtual scanning result onto the real anatomical structures.

The system can further also comprise an eye camera 21, which detects any movements of the eyes and/or the head of the person conducting the scan relative to the detection unit 20 and the screen 40. If, for example, the distance between the head and the screen 40 is changed, a display must also be adapted accordingly. If the viewing direction changes, the display may have to be changed as well.

The system may also include optional position sensors 22, which detect movements of the user and help to display the contents of the screen 40 in a stable manner.

In particular, the system comprises a scanner 10, which is configured as a two and/or three-dimensional, digital recording device. This can be executed in a variety of ways. The two-dimensional image can be obtained by means of an intraoral camera, for example. The three-dimensional model can be recorded with triangulation under structured illumination, with stereo cameras, confocally, by means of time-of-flight or other principles.

As shown in FIG. 1, the system according to the invention in particular also comprises a computing unit 30, which connects the scanner 10, the screen 40 and the detection unit 20, as well as an eye camera 21 and position sensors 22, to one another. The computing unit 30 determines the superposition of scanning result and the live view, taking into account the viewing angle of the user.

According to the invention, in particular the use of a video-capable 3D surface imaging for the real-time superimposition of the live view with recorded 3D data, using the recording device to determine the transformation chain between 3D data and user field of view, is possible.

Figure 4:
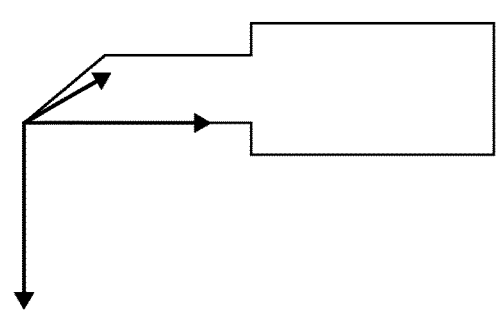
FIG. 4 shows a coordinate system of a captured scans according to the present invention.
Figure 5:
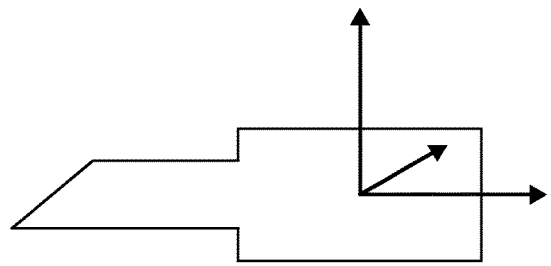
FIG. 5 shows a coordinate system of the scanner according to the present invention.
Figure 6:
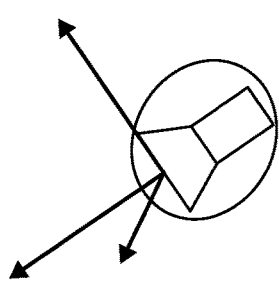
FIG. 6 shows a coordinate system of the detection unit according to the present invention.
Figure 7:
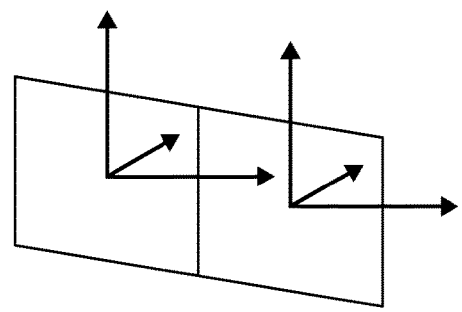
FIG. 7 shows the coordinate systems of the screen for a left eye and a right eye of a person conducting the scan according to the present invention.
Figure 8:
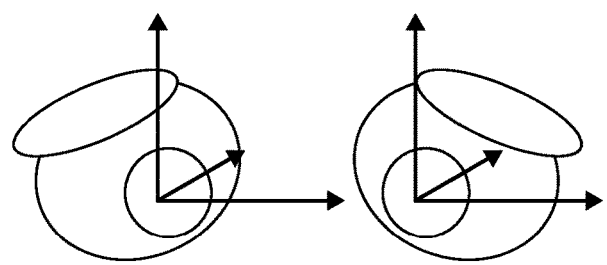
FIG. 8 shows coordinate systems of an observer as a person conducting the scan for a left eye and a right eye of the person conducting the scan according to the present invention.

As is evident from FIGS. 4 to 8, there are different coordinate systems in the system according to the invention. A coordinate system shown in FIG. 4 is determined by means of the recorded scan, the result of the intraoral scanner. A further coordinate system is the coordinate system of the scanner 10, which is shown in FIG. 5. A further coordinate system is a coordinate system of the detection unit 20 (also referred to interchangeably as an overview camera, two-dimensional overview camera and extraoral detection unit), which detects the position of the scanner 10 and is shown in FIG. 6. Another coordinate system is the coordinate system of a space shown in FIG. 7, as seen by the user or the person conducting the scan, such as for example a dentist, wherein there is a system for each eye, i.e. two systems. Finally, there is also a coordinate system of the observer, which is shown in FIG. 8.

Figure 3:
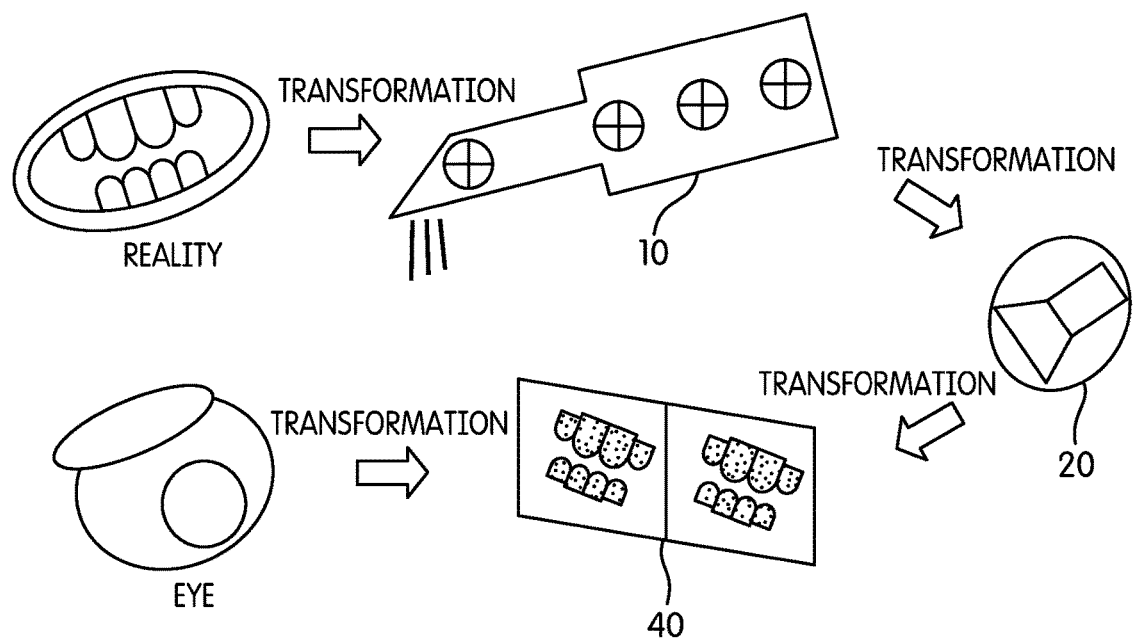
FIG. 3 shows an overview of the imaging chain of the system according to the present invention.

In order to precisely superimpose an image captured by the scanner 10 as a virtual content over anatomical structures captured by the overview camera 20 as the live view, as is shown in FIG. 2, a number of known transformations between the previously specified coordinate systems are necessary, as can be seen, for example, in FIG. 3.

A transformation concerns a transformation of the live view to the screen 40.

Another transformation relates to a transformation of the live view to the scanner 10, which is known during scanning. The scanner 10 creates the relationship between the live view and the digital model with an accuracy that is typically very high.

Figure 10:
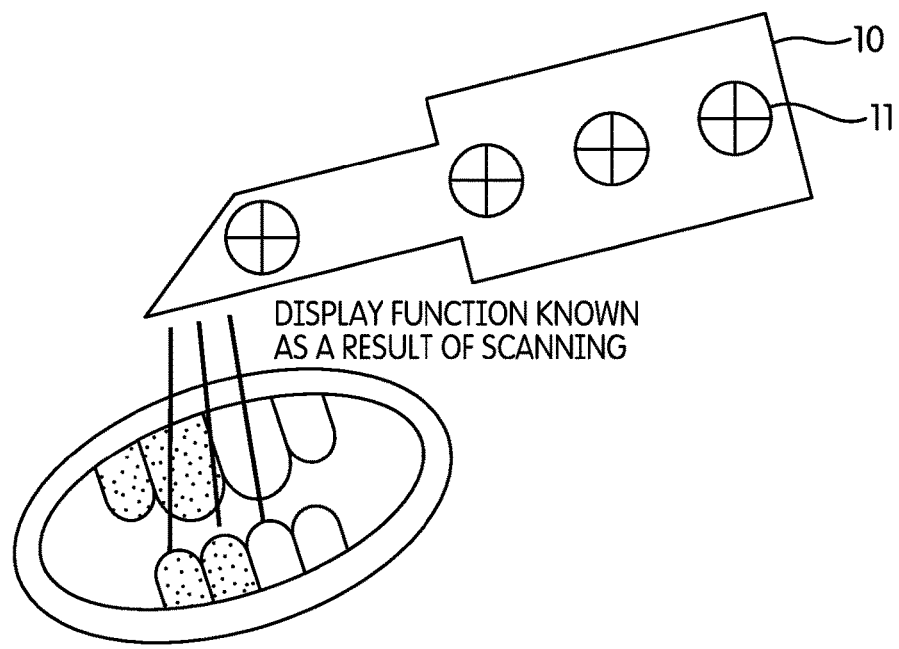
FIG. 10 shows a creation of a correlation between real teeth and a virtual model of the teeth with position markers on the scanner according to the present invention.

Another transformation relates to a transformation of the scanner 10 to the overview camera. The position of the scanner 10 can be determined by easily recognizable position markers 11 on the scanner 10. These position markers 11 can also be any kind of illustration with a known texture, such as a company or product logo. These position markers provide information about the position and size of the scanner 10, because they are mounted on the scanner 10 in a known geometry and size, as can be seen in FIG. 10. The position of the scanner 10 can thus also be sufficiently detected by means of a two-dimensional overview camera. The optical position markers can, for example, be known textures and can be tracked in accordance with "M. Ozuysal et al.: Feature Harvesting for Tracking-by-Detection, European Conference on Computer Vision, 2006". Special position markers can be tracked, for example, in accordance with "D. Wagner et al.: Robust and Unobtrusive Marker Tracking on Mobile Phones, Technical Report, Graz University of Technology".

Another transformation relates to a transformation of the overview camera to the screen 40. This correlation can be determined in a stable manner in advance, for example by means of a fixed geometry of the overview camera to the screen 40.

Another transformation relates to a transformation of the eye of a person conducting the scan to the screen 40. This correlation is different from person to person and has to be determined by means of a personal calibration prior to a first use. Since the eyes move and the viewing direction can change, depending on the system, the eyes have to be tracked as well; this can be done with the already mentioned eye camera 21.

This imaging chain can be calculated, for example, with transformations in homogeneous coordinates. A linear transformation T of a coordinate vector $\vec{x}$ can be expressed in linear algebra in matrix form, wherein A represents the imaging matrix:

$$T(\vec{x}) = A\vec{x}$$

A successive execution of linear images corresponds to the matrix product of the associated imaging matrices.

Further details can be found in the literature, for example in "Hartley and Zissermann: Multiple View Geometry in Computer Vision, Cambridge University Press".

In order to avoid the determination of the position of the eye, the validity range of a calibration can, for example, be restricted to an average spatial angle of the field of view of a user or a person conducting the scan. If a user turns his head in such a way that the geometry to be displayed leaves this spatial angle, the superposition can be hidden.

The various coordinate systems are converted into one another using suitable coordinate transformations (transformation instructions). Lastly, there is a transformation instruction that performs the above transformations in one step for each eye respectively; this means that two transformations are performed. The transformation specification allows the movements of teeth as an anatomical structure of a patient to be converted into the coordinate system of a respective eye of a user, and allows 3D geometries recorded by the scanner 10 to be displayed on the screen 40 in the correct position with respect to an image naturally seen by the eye.

Figure 9:
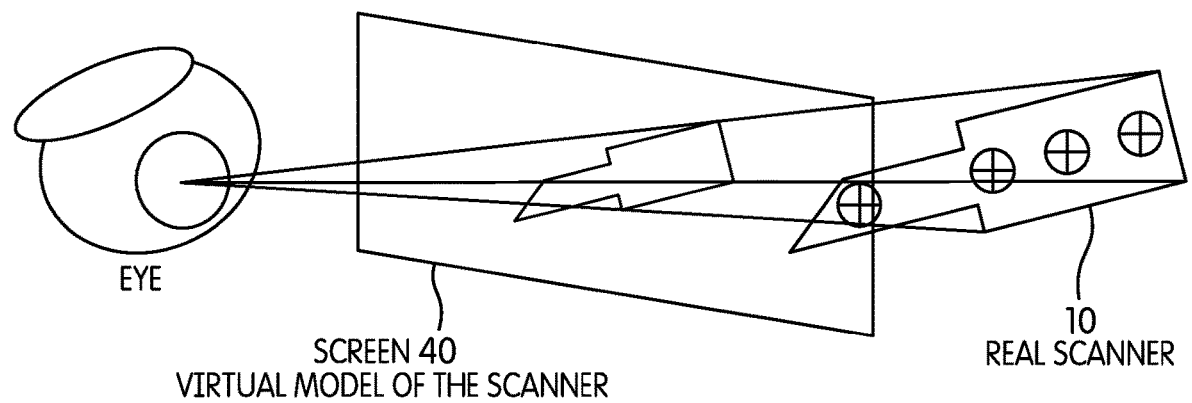
FIG. 9 shows a calibration according to the present invention.

In order to calibrate the entire system (in particular eye to screen), the scanner 10, for example, can be aligned in such a way that it conforms to the virtual display of the scanner 10, as can be seen in FIG. 9. If the imaging chain is interrupted, such as by a faulty scan, a registration error or a masking of the scanner 10, for example, the virtual content is displayed at the best possible position.

This Position is Preferably Determined by Means of:

Acceleration sensors that are mounted on the scanner 10. These allow a short-term estimation of the position of the scanner 10. For longer periods, however, small errors add up and the estimated position thus becomes less accurate.

Tracking an anatomical structure to be scanned. The teeth of the upper jaw of a patient are fixedly connected to his head. The observation of facial features, such as the eyes, can provide information regarding the location of the teeth.

Depending on the resolution of the overview camera and a distance to the anatomical structure, such as to the teeth of a patient, for example, features on the teeth can be recognized as well. The correlations of 2D features to a 3D model position can be learned during a successful scan. Such features can, for example, be specific edge patterns or even a color distribution of the teeth.

Faulty observations can be included in a movement model of teeth as an anatomical structure, such as in a Kalman filter for example, in order to calculate a stable estimation of the position with the computing unit. This can be performed in a manner similar to that of a position estimation of a car in the case of a GPS signal loss.

The content of the screen 40 will be addressed in the following.

Figure 11:
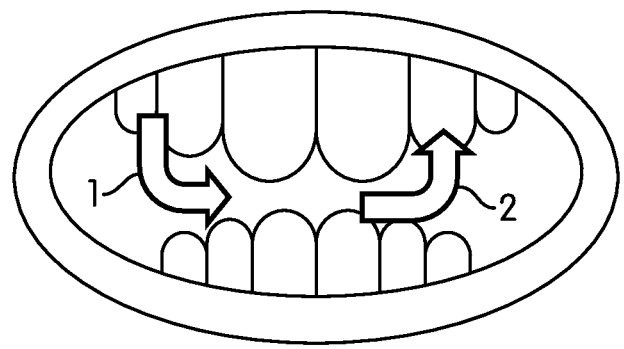
FIG. 11 shows a superimposed, standardized scanning guide for obtaining reproducible scanning results according to the present invention.
Figure 12:
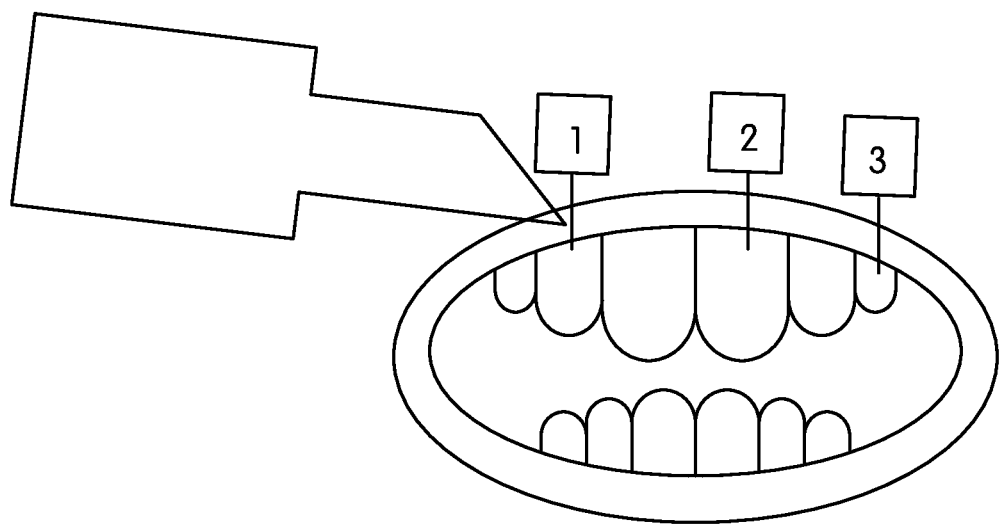
FIG. 12 shows superimposed markings, which disappear after successful detection, according to the present invention.

In order to increase the reproducibility of the scanning results, scan protocols can be superimposed during routine scanning. From "Ender and Mehl: Influence of scanning strategies on the accuracy of digital intraoral scanning systems, International Journal of Computerized Dentistry, 2013," for example, it is known that scan protocols can increase the accuracy of the model. Such protocols are usually taught to users in a training phase. The proposed system makes it possible to suggest and superimpose such scan protocols directly during scanning. These instructions can be applied easily, because the correlation between the scanner and the model is obvious. The scan protocols do not have to be permanently established in advance, but can also be suggested interactively in order to minimize registration errors. To correct small registration errors, loop closing is usually particularly important; see for example: "T. Weise et al.: In-hand Scanning with Online Loop Closure, ICCV Workshops, 2009". The system can suggest specific, particularly valuable loop closures, in order to improve the accuracy of the model. The scanning guide can be realized by means of arrows, for example, that indicate the scanning direction, as can be seen in FIG. 11. It is also conceivable to superimpose numbered orientation points as an aid. These orientation points disappear as soon as this region has been successfully scanned. This option can be seen in FIG. 12.

Figure 13:
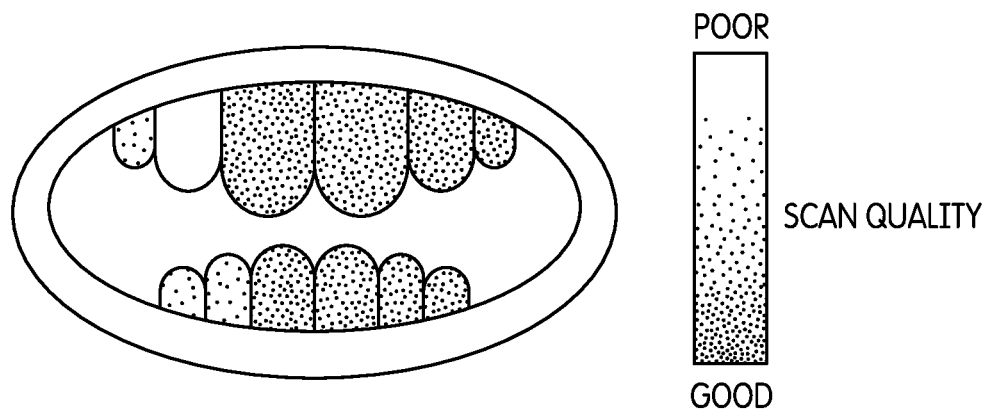
FIG. 13 shows a superimposed indication of gaps in the model or low point density according to the present invention.

As a further aid, the quality of a scan can be superimposed virtually, with specific coloring for example, as can be seen in FIG. 13. The quality of the scans is poor, for example, if there are gaps in the model. These regions can then be suggested as the next regions to be scanned.

Figure 14:
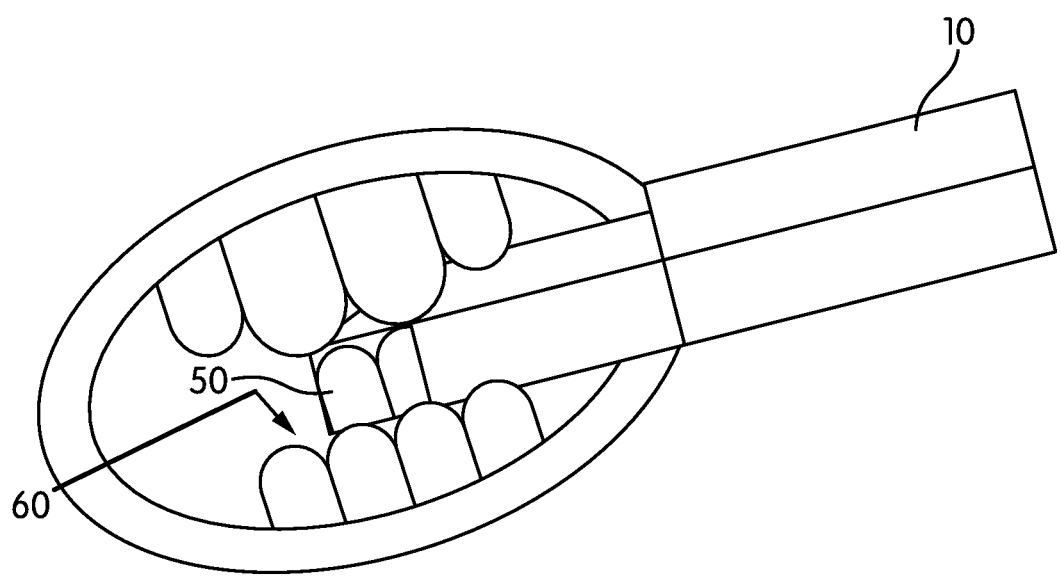
FIG. 14 shows a display of an image of the intraoral scanner near the head of the scanner according to the present invention.

In order to visualize not directly visible views of the model, the scanner 10 functions as a virtual mirror 50. The view that is not visible from a user's point of view is virtually mirrored near the head of the scanner 10, as shown in FIG. 14. The mirror is virtual and can therefore be positioned as desired, such as according to FIG. 14 directly on the scanner 10, for example, or even next to the scanner 10. If necessary, the mirror can also function as a magnifying glass or a magnifying concave mirror.

It is also possible to include another virtual magnifying glass to be able to display critical regions in an enlarged manner.

If the scanner 10 has the capability to record two-dimensional scans, the virtual mirror can also function as an electronic dental mirror of the model or of the real teeth. In the event that there are existing 3D scanning results, these are used to display the model data relative to the position of the scanner 10. Without 3D scanning results, the virtual dental mirror directly displays the two-dimensional scan relative to the position of the scanner 10.

The image of the displayed scan is displayed by introducing an artificial illumination. The corresponding virtual light source is preferably positioned where a dentist as the person conducting the scan typically has his light positioned, such as on his forehead for example. In order to be able to position this virtual light source correctly, the system has to know the relative position of the dentist to the patient. In the simplest case, the overview camera is rigidly connected to the head of the dentist. The image correlation between the overview camera and the teeth of a patient is known as a result of the scanning.

Visualization has to take place in real time, namely ideally with a latency of at most 0.1 seconds. Higher latencies do not generally limit the applicability of the method, but a user is forced into a correspondingly slower handling of the scanner 10. Latency cannot be completely avoided because, to determine the position of the scanner 10, the 3D image has to be generated first and registered to the other geometry to be displayed (conversion to a common coordinate system).

Visualization with short latency requires correspondingly powerful computing hardware. The computer hardware can be dispersed. Therefore, there can be a CPU and a GPU between the screen 40 and the detection unit 20. There can be additional CPUs and GPUs in the computing unit 30, which connects the screen 40, the detection unit 20 and the scanner 10.

The spatial arrangement of the virtual model and the live view will be discussed now.

In order to display the virtual model of teeth as an anatomical structure as naturally as possible and positioned correctly in the mouth, the objects in the immediate vicinity of the teeth must be segmented. This segmentation can be carried out, for example, by the correlation of the optical flow of the virtually covered real teeth and the virtual model. The optical flow of the covered 2D view has to coincide with the flow of the estimated virtual model. If this is not the case, these moving interferences are displayed spatially in front of the virtual model. If the intraoral scanner also supplies an RGB image and the virtual model can be colored in this way, the color deviations between the real teeth and the model could also be used for segmentation. If the color values do not match, for example, the virtual model is not displayed in these regions.

This option can selectively also be switched off; for example to display gaps in the model behind the head of the scanner 10.

In particular, during pauses in the scanning procedure, the position, orientation and scaling of the anatomical structures are estimated by the computing unit 30 by means of tools. A distinction can be made between invasive and non-invasive methods, whereby the non-invasive methods are preferred.

An invasive method is the attachment of markers or some other tracking sensor on the anatomical structure to be scanned. A non-invasive method is the pairing of optical 2D or 3D properties of the anatomical structure. 2D or 3D properties can for example be a sparse number of eye-catching, local points or even a number of larger regions that are densely distributed over the object.

Examples of Local 2D Properties are:
Local color differences on anatomical structures. In the described application these are typically tooth-gum transitions.
Local brightness differences. In the described application these are typically fine brightness differences on teeth.
Points of maximum brightness
Points of minimum brightness
Examples of Local 3D Properties are:
Local shape differences on anatomical structures that can be described with degrees of curvature, for example.

In order to achieve a more robust description, local 2D or 3D properties can additionally be examined with respect to their spatial distribution. The proximity relationships between local points can be described by means of distance measures, for example.

One option is to align the properties on the virtual model with the properties that are captured by the overview camera. The overview camera typically also provides 2D color data or 3D data of the surroundings. The alignment of the properties is easier, the more similar the recording conditions of the intraoral camera during the continuous scanning procedure and the overview camera during pauses in the scanning procedure are. Any illumination that is required to record the scans can thus be switched off during the recording of the images by means of the overview camera. Additional illumination can also advantageously be mounted at a location similar to that of the overview camera.

Another option is to record the closer surroundings of the anatomical structures, and to infer the anatomical structures from that information. For example, the head or parts of the head can be used to determine the parameters of the teeth. Here too, there are invasive and non-invasive methods. Markers, for example, can be attached invasively to the face. Specific viewpoints or a face mask, for example, can be tracked non-invasively.

In order to position the virtual model as precisely as possible over the real anatomical structures even during pauses in the scanning procedure, during scanning with the scanner 10 there is an automated learning phase with the method described during the generation of an image as a supervisor. During scanning and successful addition of the scan to the model, therefore, the data from the overview camera is continuously analyzed and evaluated, in order to later, during pauses in the scanning procedure, superimpose the virtual model as correctly as possible onto the real anatomical structures. In this learning phase, it is automatically detected which of the properties that are being tracked by the overview camera can be used to estimate the position, orientation and scaling of the virtual model. These properties should, for example, enable tracking that is as stable as possible. From among numerous described properties, such as local 2D or 3D properties, those are selected that, in said situation, can be tracked in a particularly stable and robust manner. With the automated learning phase, it is possible to select any desired combination of different properties present, for example, on the anatomical structures and in the vicinity thereof.

These properties should also be meaningful with respect to the estimation parameters. The relationship between the selected properties and the estimation parameters known during scanning is learned. If certain properties are not useful for estimating the desired parameters, this is identified during scanning and these properties can be ignored later in pauses in the scanning procedure.

In the event that a scan is interrupted, these skillfully selected properties are used to estimate the now unknown parameters.

The properties that are suitable for estimating the desired parameters are learned automatically. Therefore these properties do not have to be selected in advance. Instead they are adaptively adjusted from scanning procedure to scanning procedure. By means of the automated learning phase, it is possible to align properties, which are present only in the vicinity of the scanned anatomical structures, with the estimation parameters. The relationship between the position, orientation and scaling of the virtual model relative to the position, orientation and scaling of a face mask (tracked by means of the overview camera), for example, can thus be learned. The face mask can continue to be tracked during interruptions in the scanning procedure, and the anatomical structures can be displayed at the learned position, orientation and scaling relative to the face mask.

If the scanner cannot be used as an aid, the virtual model can also be positioned manually by the user via the real anatomical structures. In this manual calibration step, the relationship between the tracked properties and the position, orientation and scaling of the virtual model can then be learned as well. The manual calibration step can be performed once or also repeatedly in order to achieve a higher degree of robustness.

The present invention in particular demonstrates a system and a method for scanning anatomical structures and for visualizing the scanning result, which, with simple operation, provide an improved visualization of scanning results.

The invention claimed is:

1. A system for scanning anatomical structures and for visualizing a scanning result during a scanning procedure, wherein the system comprises the following:
an intraoral scanner configured to intraorally capture an image of the anatomical structures, wherein the intraoral scanner includes an at least one optical position marker attached thereto;
a detection unit, which is configured to track a spatial position of the intraoral scanner and determine said tracked spatial position of the intraoral scanner relative to a user conducting the scan using data associated with the at least one optical position marker; and
a computing unit having at least one processor, wherein the at least one processor is configured to:
communicatively connect the scanner, a screen, and the detection unit, wherein the screen is integrated into a pair of augmented reality glasses configured to be worn by user conducting the scan,
generate the scanning result, based on the intraorally captured image of the anatomical structures and the tracked spatial position of the intraoral scanner relative to the user conducting the scan,
wherein the at least one processor of the computing unit is further configured to automatically estimate a position, orientation, and scaling of the anatomical structures, wherein the position, orientation, and scaling of the anatomical structures are estimated in response to at least one pause in the scanning procedure, and
display, during the scanning procedure, the generated scanning result on the screen,
wherein the at least one processor of the computing unit is further configured to place the scanning result in a field of view of the user conducting the scan such that the scanning results appear superimposed on the anatomical structures in the field of view of the user. Wherein the field of view is in front of the user conducting the scan and the field of view includes a view of the anatomical structures, wherein superimposition of the scanning results on the anatomical structures in the field of view is, based on transformation processing of a plurality of coordinate systems including:
(i) a first transformation from a coordinate system of the scanner to a coordinate system of the detection unit, and
(ii) a second transformation from the coordinate system of the detection unit to a coordinate system of the screen;
wherein the scanning result is electronically communicated by the computing unit to the screen to display the generated scanning result during the scanning procedure and the at least one processor of the computing unit is further configured to perform an automated learning phase comprising a continuous analysis and evaluation of data communicated by the detection unit to generate stable tracking information of the intraoral scanner.

2. The system according to claim 1, wherein the screen is further configured to be positioned directly in a field of view of the user conducting the scan,
wherein the detection unit is an overview camera configured to generate a two- and/or three-dimensional overview image, and
wherein the overview camera is in direct proximity to the screen and is rigidly connected thereto.

3. The system according to claim 2, wherein the detection unit is rigidly mounted to the screen.

4. The system according to claim 2, further comprising an eye camera configured to detect eye movements and/or head movements of the user conducting the scan relative to the detection unit and the screen, wherein the generated scanning result displayed on the screen as a superimposed image is adapted to the eye movements and/or the head movements of the user conducting the scan by the at least one processor of the computing unit.

5. The system according to claim 4, further comprising position sensors that detect positional movements of the user conducting the scan, wherein the computing unit is further configured to include the detected positional movements in the generation of the superimposed image displayed on the screen.

6. The system according to claim 1, wherein the plurality of coordinate systems further include a common coordinate system of the screen representing both a left eye and a right eye of the user conducting the scan, and a respective left coordinate system corresponding to the left eye and a respective right coordinate system corresponding to the right eye of the user conducting the scan.

7. The system according to claim 1, wherein the screen is further configured to display information related to successful scanning.

8. The system according to claim 1, wherein the computing unit is further configured to process the image of the anatomical structures intraorally captured by the intraoral scanner and to display the image of the anatomical structures on an additional screen positioned on a distal end of the intraoral scanner, wherein the additional screen is configured to display the image of the anatomical structures as a virtual mirror of the anatomical structures.

9. The system according to claim 1, wherein the estimated position, orientation, and scaling of the anatomical structures are estimated using a non-invasive method, wherein the non-invasive method includes a pairing of optical two-dimensional or three-dimensional properties of the anatomical structure.

10. The system according to claim 9, wherein, the computing unit is further configured to process a virtual model through a learning phase, wherein the virtual model includes a plurality of additional of scans successfully added to the virtual model wherein the virtual model is displayed during the pauses in the scanning procedure, wherein transformations between the virtual model and the properties on the anatomical structures or in proximity thereto are known or are learned during a successful scan, and wherein two or three dimensional properties are selected to track the virtual model in a stable and robust manner during the pauses in the scanning procedure.

11. A method for scanning anatomical structures and for visualizing a scanning result, comprising the steps of:
   capturing at least one image of a plurality of images of the anatomical structures with an intraoral seamier in a scanning procedure, wherein the plurality of images of the anatomical structures include a plurality of individual images of the anatomical structures, wherein the intraoral scanner includes a plurality of position markers mounted thereon,
   tracking a spatial position of the intraoral scanner with a detection unit by racking the plurality of position markers mounted to the intraoral scanner,
   estimating, responsive to at least one pause in the scanning procedure, a position, orientation and scaling of the anatomical structures to generate the scanning result corresponding to the estimation, the scanning result being generated on a screen integrated into a pair of augmented reality glasses configured to be worn by the user conducting the scan;
   performing, with a computing unit comprising at least one processor, a placement of the scanning result in a field of view of a user conducting the scan such that the scanning results appear superimposed on the anatomical structures in the field of view of the user conducting the scan, wherein the field of view is in front of the user conducting the scan and the field of view includes a view of the anatomical structures, wherein superimposition of the scanning results on the anatomical structures in the field of view is based on transformation processing of a plurality of coordinate systems by the at least one processor of the computing unit, the transformation processing including:
   (i) obtaining a first transformation from a coordinate system of the scanner to a coordinate system of the detection unit, and obtaining a second transformation from the coordinate system of the detection unit to a coordinate system of the screen and
   (ii) executing an automated teaming phase comprising a continuous analysis and evaluation of data communicated by the detection unit to generate stable tracking information of the intraoral scanner,
   wherein the scanning result is electronically communicated by the computing unit to the screen to display the generated scanning result during the scanning procedure, and,
   wherein the spatial position of the scanner is tracked by the detection unit for the transformation processing to be performed by the at least one processing unit by using data received from the detection unit representing the spatial position of the scanner from the plurality of position markers mounted to the scanner.

12. The method according to claim 11, wherein the at least one processor of the computing unit is further configured to generate the scanning result by merging the plurality of individual images of the anatomical structures captured by the intraoral scanner.

13. The method according to claim 11, wherein the at least one image of the anatomical structures is captured by the intraoral scanner and/or the scanning result is/are displayed on the screen relative to the position of the scanner.

14. The system according to claim 1, wherein the computing unit is further configured to estimate the position, orientation and scaling of the anatomical structures using an anatomical marker or a tracking sensor configured to be invasively attached to the anatomical structures, wherein the anatomical market is included in the generated scanning result, during a scanning procedure.

15. The system according to claim 1, wherein the transformation includes a transformation from a coordinate system of a video of a view surrounding the user performing the scan to the coordinate system of the screen.

16. The system according to claim 1, wherein said optical position marker further provides information about a size of the intraoral scanner.

* * * * *